United States Patent [19]

White et al.

[11] Patent Number: 4,920,738
[45] Date of Patent: May 1, 1990

[54] APPARATUS FOR WINDING OPTICAL FIBER ON A BOBBIN

[75] Inventors: James C. White, Decatur; George T. Pinson, Huntsville, both of Ala.

[73] Assignee: The Boeing Company, Seattle, Wash.

[21] Appl. No.: 407,713

[22] Filed: Sep. 14, 1989

Related U.S. Application Data

[63] Continuation of Ser. No. 180,337, Apr. 11, 1988, abandoned, which is a continuation-in-part of Ser. No. 32,243, Mar. 3, 1987, Pat. No. 4,746,080.

[51] Int. Cl.⁵ .............................................. B65H 55/04
[52] U.S. Cl. ..................................... 57/62; 242/18 R; 242/158 R; 242/159
[58] Field of Search ........................................ 57/59–64, 57/264, 80, 81; 242/18 R, 158 R, 159

[56] References Cited

U.S. PATENT DOCUMENTS

| | | | |
|---|---|---|---|
| 3,319,070 | 5/1967 | Schneider | 242/158 R |
| 3,383,851 | 5/1968 | Hickman | |
| 3,543,503 | 12/1970 | Watabe et al. | |
| 3,545,192 | 12/1970 | Hickman | |
| 3,559,917 | 2/1971 | Mackie | 242/159 |
| 3,715,877 | 2/1973 | Akachi | 57/67 X |
| 3,782,096 | 1/1974 | Karlson | 57/71 |
| 3,785,137 | 1/1974 | Karlson | 57/71 |
| 3,814,348 | 6/1974 | Johnson | 242/158 R |
| 3,848,405 | 11/1974 | Karlson | 57/71 |
| 3,876,167 | 4/1975 | Nittschalk et al. | 242/158.4 |
| 4,114,821 | 9/1978 | Thoma et al. | 242/43 R |
| 4,410,147 | 10/1983 | Seibert | 242/158 R |
| 4,434,945 | 3/1984 | Hamane et al. | 242/7.14 |
| 4,456,199 | 6/1984 | Seibert | 242/158 R |
| 4,535,955 | 8/1985 | Custer | 242/158 R |
| 4,570,875 | 2/1986 | Buluschek | 242/158 R |
| 4,597,255 | 7/1986 | Hunter et al. | 57/62 |
| 4,629,145 | 12/1986 | Graham | 242/158 R |
| 4,655,410 | 4/1987 | Ruffin et al. | 242/158 R |
| 4,695,010 | 9/1987 | Smith | 242/158 R |

FOREIGN PATENT DOCUMENTS 0043366 6/1981 European Pat. Off. .
2143870A 7/1984 United Kingdom .
2182360A 10/1986 United Kingdom .

Primary Examiner—Stuart S. Levy
Assistant Examiner—Steven M. duBois
Attorney, Agent, or Firm—Finnegan, Henderson, Farabow, Garrett & Dunner

[57] ABSTRACT

The apparatus for winding optical fiber on a bobbin in axially compact coils includes a bobbin mount reciprocably driven along the fiber deployment axis, a winding arm for receiving optical fiber being fed along the deployment axis, and a supply reel for feeding optical fiber along the deployment axis with the reel being mounted on a twist arm, with the reel axis orthogonal to the deployment axis, for rotating the reel a preselected amount for each turn of the winding arm. An optical time domain reflectometer continuously monitors optical signal attenuation through the free start end of the fiber, and an optical scanner continuously scans the formed coils for the presence of gaps and overlaps. A controller is used to automatically stop, rewind, and adjust the winding apparatus when excessive signal attenuation, gaps or overlaps are detected.

20 Claims, 1 Drawing Sheet

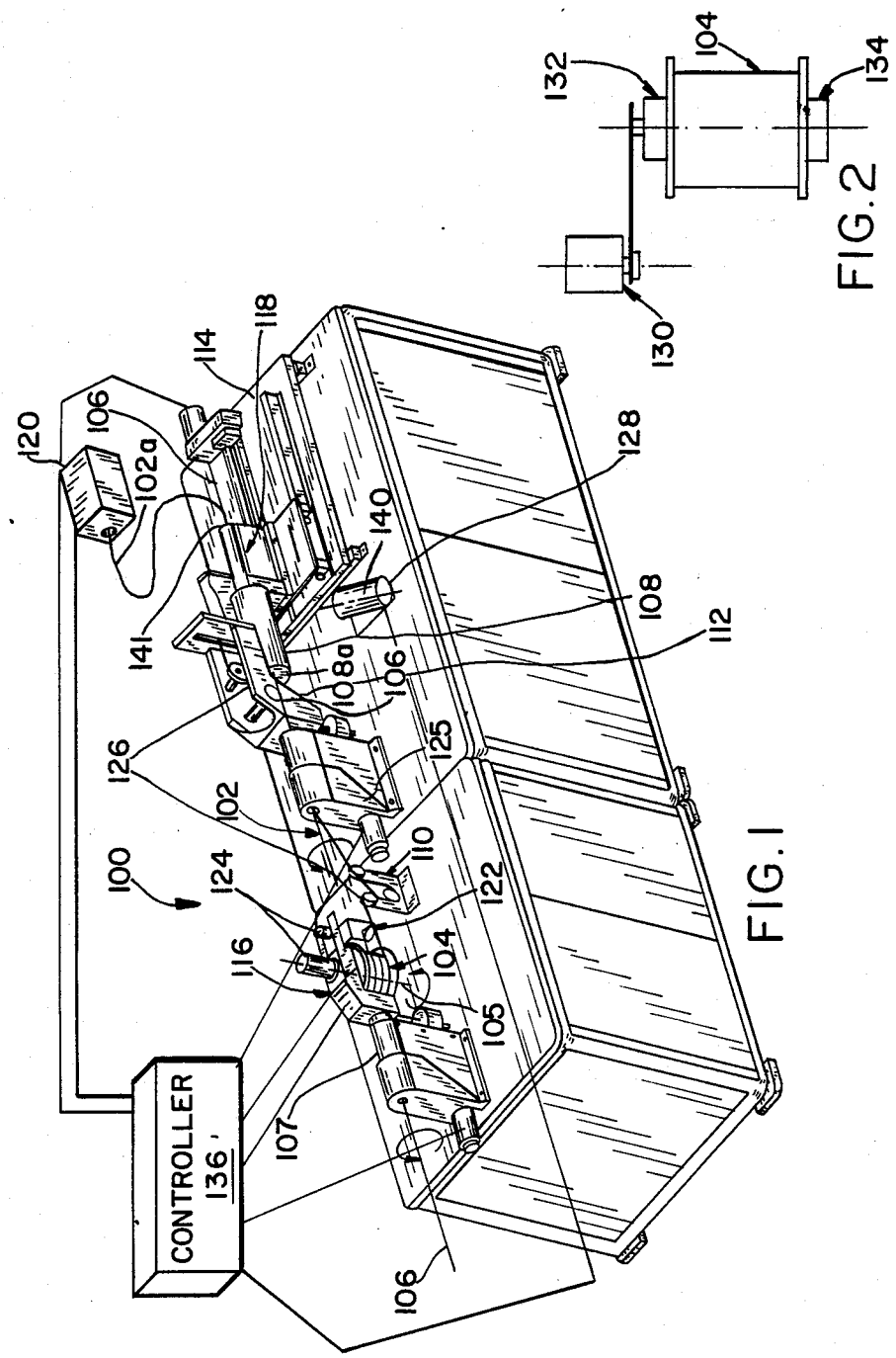

APPARATUS FOR WINDING OPTICAL FIBER ON A BOBBIN

BACKGROUND OF THE INVENTION

This application is a continuation of application Ser. No. 180,337, filed Apr. 11, 1988, now abandoned, which is a continuation-in-part of application Ser. No. 032,243 filed Mar. 3, 1987, now U.S. Pat. No. 4,746,080.

FIELD OF THE INVENTION

The invention relates to apparatus for winding optical fiber on a bobbin and, more particularly, to apparatus for winding optical fiber on a bobbin in a configuration which permits free streaming of the fiber from the bobbin without clumping or knotting and which minimizes adverse effects of the winding on the optical signal passing through the fiber.

DESCRIPTION OF RELATED ART

A number of weapons and communications systems have been developed or are under development which use an optical fiber for two-way data communication between two or more moving bodies or between a moving body and a fixed station. Examples of such uses include communication links between aircraft, between an aircraft and a ship, and between a projectile, such as a missile or mortar shell, and a control station at its launch site. As an example of the latter use, see U.S. Pat. No. 4,746,080 to Pinson. Use of optical fiber for such communication precludes electromagnetic interference and compromising interception.

Optical fiber, however, has certain disadvantages not present in other forms of communication. Optical fiber is fragile rendering it subject to breakage while a wire communication system is stronger. Aside from breakage, optical fiber communication performance may be degraded by microcracks or microbends in the fiber generated by bending or other stresses imposed on the fiber. Such damage to an optical fiber not only reduces the fiber's long-term durability, but also causes losses in optical signal strength and content.

A typical optical fiber application involves packaging a continuous length of optical fiber inside a vehicle with one end of the fiber being attached to operational devices in the vehicle, attaching the other end of the fiber to a control or communications station at the launch site, launching the vehicle, and conducting two-way communication with the vehicle during its flight.

The problem is to provide a reliable and compact means for packaging the optical fiber in the vehicle which will minimize stresses on the fiber to preclude adverse effects on communication performance and which will permit reliable deployment of the fiber during flight of the vehicle. The use of wire for guidance or control of launched vehicles is known. U.S. Pat. No. 3,114,456 to Billiard, U.S. Pat. No. 3,156,185 to Hermann et al. and U.S. Pat. No. 3,319,781 to Simpson et al. are examples of such uses. The devices of these patents, however, are not directed to use of optical fiber as the communication medium. As noted above, the characteristics of optical fiber present difficulties not involved in use of wire for communication. The patents do teach the use of bobbins on which the wire is wound, but the fragility of optical fiber requires specialized winding on a bobbin that minimizes communication losses as well as permitting free streaming from the vehicle without clumping or knotting.

The subject invention provides an apparatus for winding a continuous length of optical fiber on a bobbin for use in a moving or launched vehicle. The winding apparatus minimizes stresses imposed on the fiber while permitting free streaming of the fiber from the vehicle. Other objects and advantages of the invention will be set forth in part in the description which follows, and in part will be apparent from the description, or may be learned by practice of the invention. The objects and advantages of the invention may be realized and attained by means of the instrumentalities and combinations particularly pointed out in the appended claims.

SUMMARY OF THE INVENTION

In accordance with the present invention, as embodied and broadly described herein, the apparatus for winding optical fiber on a bobbin comprises means for mounting the bobbin on which optical fiber is to be wound, the bobbin having a deployment axis along which the wound fiber is deployed during use, and means for supplying a strand of optical fiber along the deployment axis toward the bobbin, the fiber supply means imparting a selected twist to the fiber about the deployment axis. The apparatus also has means including a winding arm for receiving the supplied optical fiber strand along the deployment axis and rotatably winding the axially received stand in coils on the bobbin. The apparatus also can include drive means for reciprocating the bobbin mounting means along the deployment axis, the drive means cooperating with the receiving and winding means for moving the bobbin mounting means along the axis a predetermined distance for each rotation of the winding arm, for winding successive layers of axially compact optical fiber coils.

Preferably, the apparatus further includes means for controlling the tension in the optical fiber being wound on the bobbin by the winding means, a fiber supply reel with optical fiber wound thereon, and brake means for selectively releasing and stopping the supply reel. The fiber supply means further can include a fiber supply reel twist arm for mounting the fiber supply reel for rotation about the deployment axis with the axis of the supply reel being substantially orthogonal to the deployment axis and means for rotating the supply reel twist arm a predetermined amount for each rotation of the winding arm.

It is also preferred that the apparatus further include means for continuously monitoring the degree of optical signal attenuation in the fiber being wound on the bobbin. The monitoring means can include an optical time domain reflectometer.

It is still further preferred that the apparatus include means for sensing gaps and overlaps in the fiber coils wound on the bobbin. An automatic control means operatively connected to the sensing means, the winding means and the bobbin drive means also can be provided for automatically reversing the direction of rotation of the winding arm for a preselected number of turns whenever a gap or overlap is sensed, and for adjusting the predetermined distance the bobbin mounting means is moved for each rotation of the winding arm in accordance with whether a gap or overlap is sensed.

Further, in accordance with the present invention, as embodied and broadly described herein, the method for producing a bobbin wound with optical fiber comprises the steps of feeding optical fiber from a source toward the bobbin, the optical fiber having at least one free end, winding the fed optical fiber around the bobbin, and continuously monitoring the optical signal attenuation in the optical fiber through the one free end during the feeding and winding steps.

Preferably, the winding step includes the step of forming axially adjacent coils of optical fiber on the bobbin, wherein the method includes the further step of continuously sensing the formed coils for the presence of gaps and overlaps between the formed coils. It is also preferred that the winding step further includes the step of axially translating the bobbin a predetermined distance for each wound coil of optical fiber, and that the method further include the sub-steps of automatically stopping the winding whenever a gap or overlap is sensed, unwinding one or more coils from the wound bobbin, adjusting the value of the predetermined translation distance per wound coil to compensate for the gap or overlap, and resuming the winding and sensing steps.

The invention resides in the novel parts, constructions, steps, arrangements, combinations and improvements shown and described. The accompanying drawings, which are incorporated in and constitute a part of this specification, illustrate the presently preferred embodiments of the invention, and, together with the description, serve to explain the principles of the invention.

BRIEF DESCRIPTION OF THE DRAWING

FIG. 1 is a diagrammatic representation of a bobbin winding apparatus made in accordance with the present invention; and FIG. 2 is a detail view of the optical fiber supply reel support mechanism of the apparatus depicted in FIG. 1.

Reference will now be made to the present preferred embodiment of the invention which is illustrated in the accompanying drawing.

DESCRIPTION OF THE PREFERRED EMBODIMENT

The presently preferred optical fiber winding machine, generally designated 100, is depicted in FIG. 1. Winding machine 100 is intended to wind optical fiber 102 on bobbin 108. Bobbin 108 has a generally truncated conical shape. The surface of bobbin 108 may be grooved to receive the optical fiber. In use, the wound fiber is intended to stream unimpeded from the smaller radius conical end 108a along bobbin axis 106 which also represents the deployment axis.

In accordance with the present invention, the winding machine includes means for mounting the bobbin. As embodied herein, and as seen in FIG. 1, winding machine includes bobbin support 118 and bobbin drive 114. Bobbin drive 114 reciprocates support 118, and unmounted bobbin 108, along axis 106 as the optical fiber 102 is wound around bobbin 108 by means to be described hereinafter.

Further in accordance with the present invention, means are provided for supplying a continuous strand of optical fiber along the bobbin deployment axis. The fiber supply means also imparts a predetermined degree of twist to the optical fibers about the deployment axis. As embodied herein, winding machine 100 includes optical fiber supply reel 104 mounted to rotate on shaft 105. Shaft 105, in turn, is mounted on reel twist arm 116 which is rotatably supported by supply reel arm drive assembly 107 the axis of which is located along deployment axis 106. Thus, the axis of shaft 105 holding reel 104 is substantially orthogonal to axis 106.

As best seen in the detail of FIG. 2, optical fiber 102 is payed out from fiber supply reel 104 by the action of reel drive motor 130 acting through reel clutch 132. Reel brake 134 is provided to selectively release and stop reel 104 at the start and finish of the winding operation and also at certain other times in the operation of winding machine 100 as will be explained in the subsequent discussion.

In the preferred embodiment of winding machine 100, the fiber supply means also includes tension sensor 110 which provides a signal to automatic controller 136 which, in turn, controls both supply reel motor 130 and supply reel clutch 132 to impart a predetermined amount of tension to the fiber strand payed out from reel 104. Controller 136 can be a microprocessor, and those skilled in the art would be able to program controller 136 to achieve the desired tension control, given the present disclosure.

Still further in accordance with the present invention, means are provided for rotatably winding the axially fed optical fiber strand in coils about the bobbin. As embodied herein, winding means includes winding arm 112 rotatably supported on winding arm drive assembly 125. Drive assembly 125 receives fiber 102 from tension sensor 110 along deployment axis 106, and fiber 102 thereafter is passed to winding arm 112 which rotates around bobbin 108. In the depicted embodiment supply reel arm drive assembly 107 is controlled to rotate supply reel arm 116 at a predetermined rate dependent upon the rotation rate of winding arm 112. Since winding arm 112 unavoidably twists fiber 102 as it rotates around bobbin 108, the supply reel arm can be rotated in a direction to supply additional or reverse twist (untwist) to fiber 102 prior to the winding operation. In this manner, winding machine 100 controls the degree of twist actually imparted to fiber 102 as it is wound on bobbin 108. Controller 136 also can be used to control the rate of rotation of supply reel arm 107 relative to winding arm 112.

In accordance with another aspect of the present invention, the winding machine is provided with means to continuously monitor the degree of optical signal attenuation in the fiber being wound on the bobbin. As embodied herein, optical time domain reflectometer 120 is connected to the free, start end 102a of fiber 102. In the embodiment shown in FIG. 1, bobbin support 118 restrains bobbin 108 from rotating. At the beginning of the winding cycle, free end 102a is threaded to the interior of bobbin 108 and through bobbin support 118 to reflectometer 120. Reflectometer 120, in turn, is connected to controller 136 which controls both the fiber winding and fiber feed components of winding machine 100. Upon detection by reflectometer 120 of an unacceptably large degree of signal attenuation in fiber 102, controller 136 will automatically stop the fiber winding and fiber feed operations until the problem is remedied, e.g., by cutting out a faulty section of fiber 102 and splicing the cut ends.

For the intended applications of the fiber wound bobbins produced by the present invention, it is necessary to have the coils closely adjacent, that is, either abutting or slightly spaced in the direction of the deployment axis, but without overlaps between adjacent coils which could cause snagging during deployment. Therefore, in accordance with yet another aspect of the present invention, the winding machine is provided with means for continuously sensing the coils or turns of fiber wound on the bobbin to detect the presence of gaps and overlaps between adjacent coils. As embodied herein, winding machine 100 includes at least one optical scanner 128 having scanning axis 140 directed at the peripheral surface of bobbin 108. More than one scanner 128 can be used to scan the entire peripheral surface of bobbin 108, but only one scanner is shown, for clarity. Optical scanner 128 is connected to controller 136 which, as described above, also is operatively connected both to fiber supply reel motor 130 and clutch 132 and to winding arm drive assembly 125. Controller 136 also is connected to bobbin support drive 114 and, during normal operation, controls bobbin support drive 114 to translate bobbin 108 a predetermined distance for each turn of winding arm 106, in order to achieve axially abutting coils. However, upon detection of a gap or overlap on bobbin 108 by scanner 128, controller 136 will automatically stop winding arm 106 and supply reel 104, reverse the directions of rotation of winding arm 106 and supply reel 104 to unwind one or more coils from bobbin 108 and back onto supply reel 104, adjust the value of the predetermined travel distance of bobbin support drive 114 per rotation of winding arm 106, and then resume normal winding operation. In order to prevent damage to fiber 102 during rewind onto supply reel 104, level winding device 122 is provided on reel support arm 116 to guide fiber 102 from tension sensor 110 to reel 104. In this manner, no overlapping coils are formed on supply reel 104 during the rewind.

To summarize, in winding machine 100, optical fiber 102 is fed from fiber supply reel 104 along deployment axis 106, that is the same axis that the optical fiber is deployed from the bobbin when in use. Optical fiber 102 is guided to bobbin 108 via fiber tension control device 110 to winding arm 112 which rotates around bobbin 108. Bobbin 108 is moved along deployment axis 106 by bobbin drive 114 a predetermined distance for every turn of winding arm 112. Fiber supply reel 104 may be rotated around deployment axis 106 by reel twist arm 116 a predetermined amount for every turn of winding arm 112.

In winder 100, therefore, fiber 102 is wound on bobbin 108 in reverse of the manner in which fiber 102 streams from the bobbin when in use. The twist imparted to fiber 102 during the winding process using winder 100 is varied to accommodate the expected change of torsion in fiber 102 during storage of the wound bobbin and to eliminate torsional stress and twisting of fiber 102 during deployment from bobbin 108. The degree of twist is predetermined in view of the properties of the glass and/or plastic in fiber 102.

Bobbin 108 may or may not be rotated during winding. If bobbin 108 is rotated, the end of fiber 102 is threaded inside bobbin 108 to a rotating optical coupler such as coupler 141 through which fiber 102 is connected to reflectometer 120. If bobbin 108 is not rotated, the end 102a of fiber 102 is threaded into the inside of bobbin 108, through bobbin support 118, and to optical time domain reflectometer 120 as shown in FIG. 1. The latter device continuously monitors the optical characteristics of fiber 102 during winding, and if optical attenuation exceeds a predetermined value, the winding operation is stopped and the cause determined. Winder 100 permits rewinding from bobbin 108 to reel 104 over a level winding device 122 and tension control 110 which assures even rewinding. If a defect is identified, the fiber is rewound to reel 104 until the defective portion is located and the defective portion is cut out and the undamaged fiber is spliced.

Tension in fiber 102 during winding is measured by tension sensor 110 and controlled through reel drive motor 130 and clutch 132. Brake 134 is used for precision starting and stopping of reel 104. Desired winding tension is small to minimize compressive stress in fiber 102 which increase attentuation of optical signals through the fiber. Small variations in tension imposed generally at points 126 along the fiber path are removed by control of reel motor 130 and clutch 132.

Winder 100 also includes sensor 128 disposed to identify undesired gaps between fiber turns on bobbin 108 and inadvertant overwinds of the fiber during winding. Controller 136 responsive to sensor 128 provides automatic stopping, rewinding, adjusting and restarting the process in response to sensed defects.

The invention provides an apparatus for winding optical fiber on a bobbin for free streaming therefrom which minimizes the occurences of undue twisting and gaps or overlaps between adjacent coils or turns which could impede free streaming and/or cause unacceptable attentuation of optical signals through the fiber. While the presently described apparatus is useful for winding bobbins in accordance with the winding method disclosed in Ser. No. 032,243, it is not restricted to that method. It will be apparent to those skilled in the art that various modifications and variations could be made to the apparatus of the invention without departing from the scope or spirit of the invention.

What is claimed is:

1. Apparatus for winding optical fiber on a bobbin comprising:
   means for mounting the bobbin on which optical fiber is to be wound, the bobbin having a deployment axis along which the wound fiber is deployed during use;
   means for supplying a strand of optical fiber along said deployment axis toward said bobbin, said fiber supply means imparting a selected twist to the fiber about said deployment axis; and
   means including a winding arm for receiving said supplied optical fiber strand along said deployment axis and rotatably winding said axially received strand in coils on the bobbin,
   wherein said fiber supply means includes a fiber supply reel with optical fiber wound thereon, said reel having a reel axis, and wherein said fiber supply means further includes a fiber supply reel twist arm for mounting said fiber supply reel for rotation about said deployment axis with said reel axis being substantially orthogonal to said deployment axis.

2. The apparatus as in claim 1 further including means for controlling the tension in the optical fiber being wound on the bobbin by said winding means.

3. The apparatus as in claim 2 wherein said tension control means includes tension sensor means positioned to monitor the tension in the optical strand between said fiber supply means and said receiving and winding means, a supply reel drive motor, a supply reel clutch operatively connecting said motor to said supply reel, and a controller responsive to said tension sensor for simultaneously controlling said supply reel motor and said supply reel clutch to provide a predetermined tension value.

4. The apparatus as in claim 1 wherein said fiber supply means includes brake means for selectively releasing and stopping said supply reel.

5. The apparatus as in claim 1 wherein said apparatus further includes means for rotating said supply reel twist arm a predetermined amount for each rotation of said winding arm.

6. Apparatus for winding optical fiber on a bobbin comprising:
   means for mounting the bobbin on which optical fiber is to be wound, the bobbin having a deployment axis along which the wound fiber is deployed during use;
   means for supplying a strand of optical fiber along said deployment axis toward said bobbin, said fiber supply means imparting a selected twist to the fiber about said deployment axis;
   means including a winding arm for receiving said supplied optical fiber strand along said deployment axis and rotatably winding said axially received strand in coils on the bobbin;
   means for continuously monitoring the optical signal attenuation in the fiber being wound on the bobbin; and
   means responsive to said monitoring means for automatically stopping said supply means and said winding means whenever the optical signal attenuation exceeds a predetermined value,
   wherein said bobbin mounting means includes means for receiving a free fiber end from the bobbin, and wherein said monitoring means includes an optical time domain reflectometer connectable to the free fiber end received in said bobbin mounting means.

7. The apparatus as in claim 1 wherein the apparatus further includes drive means for reciprocating said bobbin mounting means along said deployment axis, said drive means cooperating with said receiving and winding means for moving said bobbin mounting means along said axis a predetermined distance for each rotation of said winding arm, for winding successive layers of axially compact optical fiber coils.

8. The apparatus as in claim 7 further including means for sensing gaps and overlaps in the fiber coils wound on the bobbin.

9. The apparatus as in claim 8 further including automatic control means operatively connected to said sensing means and said winding means for reversing the direction of rotation of said winding arm for a preselected number of turns whenever a gap or overlap is sensed, and rewinding means associated with said supply reel, and wherein said automatic control means also is operatively connected to said drive means for automatically adjusting the predetermined distance said bobbin mounting means is moved for each rotation of said winding arm in accordance with whether a gap or overlap is sensed.

10. The apparatus as in claim 9 wherein said rewinding means includes a level winder.

11. Apparatus for winding an optical fiber on a bobbin, having an outer peripheral surface, the fiber being supplied from a fiber source and having a starting end, the apparatus comprising:
    means for mounting the bobbin, the bobbin being restrained against rotational movement about the bobbin axis by said mounting means;
    means rotatable about the bobbin axis for winding the fiber around the bobbin, the starting end of the fiber being arranged to be free from the bobbin peripheral surface; and
    means operatively connected to said free starting end for monitoring the degree of optical signal attenuation in the fiber being wound on the bobbin.

12. The apparatus as in claim 11 wherein said monitoring means continuously monitors the fiber being wound.

13. The apparatus as in claim 11 wherein said monitoring means includes an optical time domain reflectometer.

14. The apparatus as in claim 11 further including automatic control means operatively connected to said monitoring means and to said winding means for stopping said winding means when the monitored signal attenuation exceeds a predetermined level.

15. A method for producing a bobbin wound with optical fiber comprising the steps of:
    feeding optical fiber from a source toward the bobbin, the optical fiber having at least one free end;
    winding the optical fiber being fed from the source around the bobbin; and
    continuously monitoring the optical signal attenuation in the optical fiber through the one free end during said feeding and winding steps.

16. The method as in claim 15 including the further step of automatically stopping the feeding and winding steps whenever the monitored optical signal attenuation exceeds a predetermined value.

17. The method as in claim 15 wherein the winding step includes the step of forming axially adjacent coils of optical fiber on the bobbin, wherein the method includes the further step of continuously sensing the formed coils for the presence of gaps and overlaps between the formed coils.

18. The method of claim 17 wherein the winding step further includes the step of axially translating the bobbin a predetermined distance for each wound coil of optical fiber, the method including the sub-steps of automatically
    (i) stopping the winding whenever a gap or overlap is sensed;
    (ii) unwinding one or more coils from the wound bobbin;
    (iii) adjusting the value of the predetermined translation distance per wound coil to compensate for the gap or overlap; and
    (iv) resuming said winding and sensing steps.

19. Apparatus for winding an optical fiber on a bobbin having an outer peripheral surface, the fiber being supplied from a fiber source and having a starting end, the apparatus comprising:
    means for mounting the bobbin;
    means for winding the fiber around the bobbin, the starting end of the fiber being arranged to be free from the bobbin peripheral surface; and
    means operatively connected to said free starting end for continuously monitoring the degree of optical signal attenuation in the fiber being wound on the bobbin.

20. The apparatus as in claim 19 wherein the bobbin is rotatable in said mounting means, the apparatus further including rotating optical coupler means for interconnecting said monitoring means and said free starting end.

* * * * *